United States Patent
Kuroiwa et al.

(10) Patent No.: US 8,927,532 B2
(45) Date of Patent: Jan. 6, 2015

(54) THERAPEUTIC AGENT AND DIAGNOSTIC AGENT FOR MITOCHONDRIAL DYSFUNCTION BRAIN DISEASES

(75) Inventors: Toshihiko Kuroiwa, Osaka (JP); Yoshinaga Kajimoto, Takatsuki (JP); Takahiro Masubuchi, Yamatokooriyama (JP); Masahiro Ishizuka, Tokyo (JP); Tohru Tanaka, Tokyo (JP)

(73) Assignee: SBI Pharmaceuticals Co., Ltd., Tokyo (JP)

( * ) Notice: Subject to any disclaimer, the term of this patent is extended or adjusted under 35 U.S.C. 154(b) by 13 days.

(21) Appl. No.: 13/613,565

(22) Filed: Sep. 13, 2012

(65) Prior Publication Data

US 2013/0011337 A1 Jan. 10, 2013

(30) Foreign Application Priority Data

Apr. 5, 2007 (JP) ................. 2007-099508

(51) Int. Cl.
| | | |
|---|---|---|
| *A61K 31/555* | (2006.01) | |
| *A61K 31/195* | (2006.01) | |
| *A61K 31/295* | (2006.01) | |
| *A61K 31/197* | (2006.01) | |
| *A61K 31/198* | (2006.01) | |
| *A61K 33/26* | (2006.01) | |
| *A61K 45/06* | (2006.01) | |
| *A61K 49/00* | (2006.01) | |

(52) U.S. Cl.
CPC ............. *A61K 31/295* (2013.01); *A61K 31/197* (2013.01); *A61K 31/198* (2013.01); *A61K 33/26* (2013.01); *A61K 45/06* (2013.01); *A61K 49/0008* (2013.01)
USPC ............................ 514/184; 514/561; 514/567

(58) Field of Classification Search
USPC .......................................... 514/184, 561, 567
See application file for complete search history.

(56) References Cited

U.S. PATENT DOCUMENTS

| 2005/0065099 A1 | 3/2005 | Walkinshaw et al. |
| 2007/0249721 A1 | 10/2007 | Ito |
| 2009/0130227 A1 | 5/2009 | Ito |

FOREIGN PATENT DOCUMENTS

| CN | 1942163 A | 4/2007 |
| EP | 0704209 A1 | 4/1996 |
| EP | 1742038 A1 | 1/2007 |
| JP | 11-501914 A | 2/1999 |
| JP | 11-116446 A | 4/1999 |
| WO | 91/01727 A2 | 2/1991 |
| WO | 9832464 A1 | 7/1998 |
| WO | 2005/105022 A1 | 11/2005 |
| WO | 2006/035678 A1 | 4/2006 |
| WO | 2006/117885 A1 | 11/2006 |

OTHER PUBLICATIONS

Office Action dated Sep. 28, 2012 issued by the Korean Intellectual Property Office in counterpart Korean Application No. 10-2009-7020513.
International Search Report dated May 13, 2008 (PCT/JP2008/055959).
Japanese Office Action dated Apr. 4, 2012 issued by the Japanese Patent Office in corresponding Japanese Patent Application No. 2007-099508.
Nou Shinkei Geka (Cranial Nerve Surgery), 29(11): 1019-1031, 2001.
Office Action dated Aug. 25, 2010 from the Russian Patent Office in Russian counterpart application No. 2009136582/15.
Office Action issued by the State Intellectual Property Office of the P.R. of China on Mar. 30, 2011 in the corresponding Chinese Patent Application No. 200880010881.8.
Office Action issued on Feb. 29, 2012 in the corresponding Chinese Patent Application No. 200880010881.8.
Supplementary European Search Report dated Jun. 17, 2010 issued in counterpart European patent application No. 08739088.6-2123.
Office Action dated Jul. 29, 2013 issued by the Canadian Intellectual Property Office in counterpart Canadian Application No. 2682855.
Communication from the Canadian Patent Office issued Jul. 17, 2014 in a counterpart Canadian Application No. 2,682,855.

*Primary Examiner* — Renee Claytor
(74) *Attorney, Agent, or Firm* — Sughrue Mion, PLLC

(57) ABSTRACT

To provide a therapeutic agent and a diagnostic agent for mitochondrial dysfunction brain diseases including cerebral infarction as a representative.

A therapeutic agent for a mitochondrial dysfunction brain disease, which comprises (A) δ-aminolevulinic acid represented by the formula (1), a derivative thereof, or a salt thereof and (B) an iron compound in combination.

$$R^2R^1NCH_2COCH_2CH_2COR^3 \quad (1)$$

wherein $R^1$ and $R^2$ each independently represents a hydrogen atom, an alkyl group, an acyl group, an alkoxycarbonyl group, an aryl group, or an aralkyl group; and $R^3$ represents a hydroxy group, an alkoxy group, an acyloxy group, an alkoxycarbonyloxy group, an aryloxy group, an aralkyloxy group, or an amino group.

3 Claims, 2 Drawing Sheets

THERAPEUTIC AGENT AND DIAGNOSTIC AGENT FOR MITOCHONDRIAL DYSFUNCTION BRAIN DISEASES

This is a Continuation of application Ser. No. 12/594,672 filed Oct. 5, 2009, which is a §371 National Stage Application of PCT/JP2008/055959 filed Mar. 27, 2008 claiming priority based on Japanese Patent Application No. 2007-099509 filed Apr. 5, 2007, the contents of all of which are incorporated herein by reference in their entirety.

TECHNICAL FIELD

The present invention relates to a therapeutic agent and a diagnostic agent for mitochondrial dysfunction brain diseases including cerebral infarction as a representative.

BACKGROUND ART

Mitochondria is an intracellular organella present in almost all eucaryotic cells and is generally contained in an amount of several hundreds to several thousands per cell. Mitochondria has an elongated elliptic structure surrounded by two layers of an outer layer and an inner layer. As its main roles, it produces adenosine triphosphate (ATP), which is an energy source of cells, through a citric acid cycle and an electron transmitting system and oxidative phosphorylation conjugating both of them and also it plays a primary role in the regulation of cell death. It is said that active oxygen is released from mitochondria to cause decrease in cell function and cell death and it has been reported that the production of active oxygen from mitochondria increases in aged animals.

Although the mechanism of onset of Alzheimer's disease has yet been unclear, there has been obtained a finding which suggests that decrease in mitochondrial function closely relates to the omission of the nerve in Alzheimer's disease. Heretofore, as brain diseases induced by mitochondrial dysfunction, there are known, in addition to Alzheimer's disease, amyotrophic lateral sclerosis (ALS); mitochondrial diseases such as mitochondrial encephalomyopathy; migraine; Parkinson's disease; Alzheimer's disease; ischemic cerebral disorders such as cerebral infarction, hypoxic encephalopathy, and cerebral arteriosclerosis; manic-depressive psychosis; chronic fatigue syndrome; intracranial hypertension induced by hydrocephalus and head injury; normal pressure hydrocephalus; cerebral vasospasm after subarachnoid hemorrhage; prevention of cerebral ischemia at surgery and intravascular surgery; and the like.

Among them, cerebral infarction accounts for about 70% of cerebral stroke and the cerebral stroke is third cause next to malignant neoplasm (cancer) and heart disease in statistics in 2004 and accounts for 12.5% of total number of death. The cerebral infarction is classified into two types depending on the way of blocking a blood vessel. There are cerebral thrombosis wherein the blood vessel undergoes arteriosclerosis and the inner cavity is gradually narrowed and blocked and cerebral embolism wherein thrombus is formed in the heart or a large blood vessel and the thrombus is carried to the brain to block a blood vessel in the brain. The cerebral cells completely died and their recovery is impossible within several minutes when the blood flow is thoroughly shut out. However, since a blood flow from the other blood vessel(s) usually remains to some extent even when one blood vessel is blocked, the blood flow is not suddenly thoroughly shut out. The brain cells gradually die from the area where the blood flow is poor during several hours from the blockage of the blood vessel. In the cerebral thrombosis, the symptoms slowly progress and are completed after 2 to 3 days in some cases but, in the cerebral embolism, the symptoms are suddenly completed and are generally severer than in the case of the cerebral thrombosis. The cerebral infarction is further roughly classified into three types in some cases. There are the following three types: (1) atherothrombotic cerebral infarction wherein a large blood vessel at the neck or in the head is blocked by arteriosclerosis, (2) lacunar infarction wherein a fine blood vessel in the brain is blocked, and (3) cardiogenic cerebral embolism wherein thrombus is formed in the heart owing to atrial fibrillation (one kind of arrhythmia), myocardial infarction, a valvular disease of heart, cardiomyopathy, and the like and reaches the brain.

At the medical examination of the brain infarction, it is important to adequately grasp the neurological symptoms and accurately diagnose a diseased site. A rough neurological examination can be performed within 5 minutes by a medical doctor but, in order to help the diagnosis and determine an adequate therapeutic strategy, examinations such as a CT examination (computer tomography), an MRI examination (magnetic resonance imaging), an ultrasonic Doppler examination, cerebral angiography, and a cerebral blood flow examination have been performed. All these examinations are preoperative diagnosis before treatments and it is a current situation that an examination method capable of judging a diseased site while an operation is performing does not exist.

The treatment of the cerebral infarction varies depending on the type of the cerebral infarction, i.e., atherothrombotic cerebral infarction, lacunar infarction, or cardiogenic cerebral embolism, period of time after its onset, and severity. As special treatments, there may be mentioned a treatment for reducing dropsy of brain, a treatment against thrombus in the blood vessel, a treatment for protecting nerve cells, and the like. As the most effective treatment, a thrombolytic therapy (tissue plasminogen activator) is employed overseas but a thrombolytic agent should be administered within 3 hours after the onset of the cerebral infarction. As a thrombolytic therapy, there is a method of finding out a site where brain blood vessel is blocked by an examination called cerebral angiography and dissolving the thrombus through insertion of a catheter into the site but it is also necessary to perform the method within 3 to 6 hours after the onset of the cerebral infarction. Furthermore, in the case where the thrombolytic therapy is not applicable, there is also a treatment of administering an antiplatelet agent or a blood coagulation inhibitor.

However, even when these treatments are performed, there are cases where some aftereffects (consciousness disorder, movement and perception disorder, higher brain function disorder, attentiveness disorder, and emotional disorder) may remain due to delay of the performance or mistake of the performance and thus it is an actual situation that a medical agent capable of treating the diseased site simultaneously to thrombolytic therapy does not exist.

On the other hand, when δ-aminolevulinic acid (ALA) or a derivative thereof is administered, it is known that derived protoporphyrin IX is accumulated in a tumor and is effective for intraoperative diagnosis and treatment (Patent Document 1 and Non-Patent Document 1). Moreover, when δ-aminolevulinic acid (ALA) or a derivative thereof is administered to the head in combination with an iron compound, it is known to exhibit a hair growth effect (Patent Document 2). However, an action of δ-aminolevulinic acid (ALA) or a derivative thereof on cerebral diseases has not been reported.

Patent Document 1: JP-A-11-501914
Patent Document 2: WO2005/105022
Non-Patent Document 1: Nou Shinkei Geka (Cranial Nerve Surgery), 29(11): 1019-1031, 2001

DISCLOSURE OF THE INVENTION

Problems That the Invention is to Solve

An object of the invention is to provide a therapeutic agent and a diagnostic agent for mitochondrial dysfunction brain diseases including cerebral infarction as a representative.

Means for Solving the Problem

Thus, the present inventors have prepared a middle cerebral artery-occluded model rat, which is an experimental model of cerebral infarction, and investigated a relationship between a cerebral infarction site and a mitochondrial activity. As a result, the mitochondrial activity has disappeared at the cerebral infarction site and the inventors have presumed that a correlation may exist between a brain cell disorder induced by cerebral ischemia such as cerebral infarction and the mitochondrial activity.

Incidentally, for using δ-ALA in the treatment of brain diseases such as cerebral infarction, it is necessary to investigate whether δ-ALA passes through blood-brain barrier (BBB) or not. Although δ-ALA passes through BBB in a cerebral tumor, it is not known whether δ-ALA passes through BBB in a normal case and in a case of cerebral infarction. When the inventors investigated whether δ-ALA passes through BBB in a normal rat and a cerebral infarction model rat or not, a metabolite of δ-ALA, protoporphyrin IX, was confirmed specifically in the cerebral infarction site by administration of δ-ALA in the cerebral infarction model rat. On the other hand, in the normal rat, no protoporphyrin IX was observed. Thus, the passage of δ-ALA through BBB has not been observed at a normal state and δ-ALA has passed through BBB in the case of brain diseases such as cerebral infarction and is metabolized to protoporphyrin only at the cerebral infarction site in the brain tissue, so that it has been found that δ-ALA can be used for diagnosis of mitochondrial dysfunction brain diseases such as cerebral infarction.

Furthermore, when δ-ALA and an iron compound are administered after middle cerebral artery is occluded in the cerebral infarction model rat, a neurological severity score (NSS), which is an indication of cerebral infarction aftereffects, is remarkably improved, so that it has been found that the combined use of the compounds is useful as a therapeutic agent for mitochondrial dysfunction brain diseases and thus the invention has been accomplished.

Namely, the invention includes the following modes.

1. A therapeutic agent for a mitochondrial dysfunction brain disease comprising:
   (A) a δ-aminolevulinic acid represented by formula (1), a derivative thereof, or a salt thereof; and
   (B) an iron compound:

$$R^2R^1NCH_2COCH_2CH_2COR^3 \quad (1)$$

wherein $R^1$ and $R^2$ each independently represents a hydrogen atom, an alkyl group, an acyl group, an alkoxycarbonyl group, an aryl group, or an aralkyl group; and $R^3$ represents a hydroxy group, an alkoxy group, an acyloxy group, an alkoxycarbonyloxy group, an aryloxy group, an aralkyloxy group, or an amino group.

2. 2. The therapeutic agent for a mitochondrial dysfunction brain disease according to the above 1, wherein (B) the iron compound is one or two or more compounds selected from ferric chloride, iron sesquioxide, iron chlorophyllin sodium, ferritin iron, ferrous citrate, sodium iron citrate, ammonium iron citrate, ferrous fumarate, ferric pyrophosphate, ferric pyrophosphate, saccharated iron oxide, iron acetate, iron oxalate, ferrous succinate, sodium iron succinate citrate, heme iron, dextran iron, iron lactate, ferrous gluconate, sodium iron diethylenetriaminepentaacetate, ammonium iron diethylenetriaminepentaacetate, sodium iron diethylenediaminetetraacetate, ammonium iron diethylenediaminepentatetraacetate, triethylenetetramine iron, sodium iron dicarboxymethylglutamate, ammonium iron dicarboxymethylglutamate, choline iron citrate, ferrous formate, ferric formate, ammonium ferric potassium oxalate, ferrous sulfate, ferric sulfate, ammonium iron sulfate, ferric carbonate, ferrous chloride, and iron oxide.

3. The therapeutic agent for a mitochondrial dysfunction brain disease according to the above 1 or 2, wherein the mitochondrial dysfunction brain disease is amyotrophic lateral sclerosis, mitochondrial encephalomyopathy, migraine, Parkinson's disease, hypoxic encephalopathy, cerebral arteriosclerosis, manic-depressive psychosis, chronic fatigue syndrome, intracranial hypertension, normal pressure hydrocephalus, cerebral vasospasm after subarachnoid hemorrhage, prevention of cerebral ischemia at surgery and intravascular surgery, atherothrombotic cerebral infarction, lacunar infarction, cardiogenic cerebral embolism, or Alzheimer's disease.

4. A diagnostic agent for a mitochondrial dysfunction brain disease, which comprises a δ-aminolevulinic acid represented by the formula (1), a derivative thereof, or a salt thereof:

$$R^2R^1NCH_2COCH_2CH_2COR^3 \quad (1)$$

wherein $R^1$ and $R^2$ each independently represents a hydrogen atom, an alkyl group, an acyl group, an alkoxycarbonyl group, an aryl group, or an aralkyl group; and $R^3$ represents a hydroxy group, an alkoxy group, an acyloxy group, an alkoxycarbonyloxy group, an aryloxy group, an aralkyloxy group, or an amino group.

5. The diagnostic agent for a mitochondrial dysfunction brain disease according to the above 4, wherein the mitochondrial dysfunction brain disease is amyotrophic lateral sclerosis, mitochondrial encephalomyopathy, migraine, Parkinson's disease, hypoxic encephalopathy, cerebral arteriosclerosis, manic-depressive psychosis, chronic fatigue syndrome, intracranial hypertension, normal pressure hydrocephalus, cerebral vasospasm after subarachnoid hemorrhage, prevention of cerebral ischemia at surgery and intravascular surgery, atherothrombotic cerebral infarction, lacunar infarction, cardiogenic cerebral embolism, or Alzheimer's disease.

Moreover, the invention includes the following modes.

6. A therapeutic method of a mitochondrial dysfunction brain disease, which comprises administering:
   (A) a δ-aminolevulinic acid represented by the formula (1), a derivative thereof, or a salt thereof and (B) an iron compound in effective amounts:

$$R^2R^1NCH_2COCH_2CH_2COR^3 \quad (1)$$

wherein $R^1$ and $R^2$ each independently represents a hydrogen atom, an alkyl group, an acyl group, an alkoxycarbonyl group, an aryl group, or an aralkyl group; and $R^3$ represents a hydroxy group, an alkoxy group, an acyloxy group, an alkoxycarbonyloxy group, an aryloxy group, an aralkyloxy group, or an amino group.

7. A diagnostic method of a mitochondrial dysfunction brain disease, which comprises administering a δ-aminolevulinic acid represented by the formula (1), a derivative thereof, or a salt thereof in an effective amount:

$$R^2R^1NCH_2COCH_2CH_2COR^3 \quad (1)$$

wherein R¹ and R² each independently represents a hydrogen atom, an alkyl group, an acyl group, an alkoxycarbonyl group, an aryl group, or an aralkyl group; and R³ represents a hydroxy group, an alkoxy group, an acyloxy group, an alkoxycarbonyloxy group, an aryloxy group, an aralkyloxy group, or an amino group.

8. A diagnostic method of a mitochondrial dysfunction brain disease, which comprises:
   administering a δ-aminolevulinic acid represented by the formula (1), a derivative thereof, or a salt thereof and (B) an iron compound,
   taking out a part of the brain from an analyte,
   treating the part of the brain with a mitochondria-active dying agent, and
   evaluating a mitochondrial activity by a dyed state:

$$R^2R^1NCH_2COCH_2CH_2COR^3 \quad (1)$$

wherein R¹ and R² each independently represents a hydrogen atom, an alkyl group, an acyl group, an alkoxycarbonyl group, an aryl group, or an aralkyl group; and R³ represents a hydroxy group, an alkoxy group, an acyloxy group, an alkoxycarbonyloxy group, an aryloxy group, an aralkyloxy group, or an amino group.

9. A diagnostic method of a mitochondrial dysfunction brain disease according to the above 8, wherein the mitochondria-active dying agent is TTC (2,3,5-triphenyltetrazolium chloride).

10. The use of (A) a δ-aminolevulinic acid represented by the formula (1), a derivative thereof, or a salt thereof and (B) an iron compound for the preparation of a therapeutic agent for a mitochondrial dysfunction brain disease:

$$R^2R^1NCH_2COCH_2CH_2COR^3 \quad (1)$$

wherein R¹ and R² each independently represents a hydrogen atom, an alkyl group, an acyl group, an alkoxycarbonyl group, an aryl group, or an aralkyl group; and R³ represents a hydroxy group, an alkoxy group, an acyloxy group, an alkoxycarbonyloxy group, an aryloxy group, an aralkyloxy group, or an amino group.

In this connection, the therapeutic agent for a mitochondrial dysfunction brain disease of the invention includes a composition for treating a mitochondrial dysfunction brain disease.

Advantage of the Invention

According to the diagnostic agent for a mitochondrial dysfunction brain disease of the invention, a diseased site can be definitely diagnosed by observing the presence of red light upon irradiation with excitation light in the event of an emergency at brain diseases such as cerebral infarction, e.g., during an operation. Moreover, according to the therapeutic agent for a mitochondrial dysfunction brain disease of the invention, by administering it after the onset of cerebral infarction, particularly using it in combination with thrombolytic therapy or the like, aftereffects such as consciousness disorder, movement and perception disorder, higher brain function disorder, attentiveness disorder, and emotional disorder can be improved.

Figure 1:
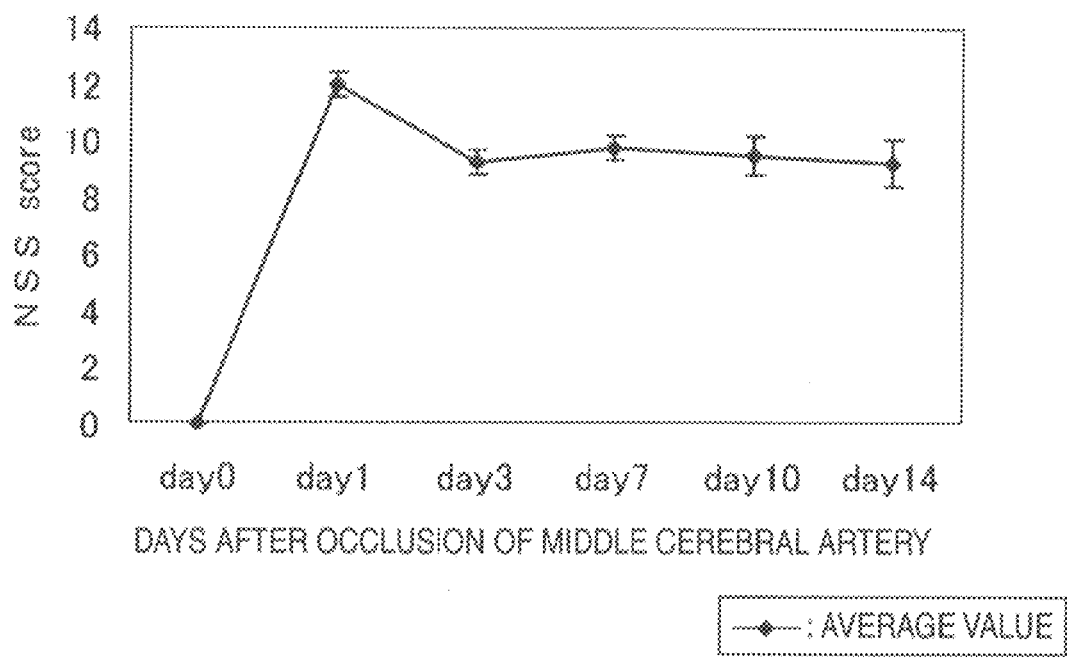
FIG. 1 is a figure showing a change of neurological severity score (NSS score) in a cerebral infarction model rat.

BEST MODE FOR CARRYING OUT THE INVENTION (A) δ-ALA or a derivative thereof for use in the therapeutic agent and the diagnostic agent for a brain disease of the invention is represented by the above formula (1). In the formula (1), as the alkyl groups represented by R¹ and R², a linear or branched alkyl group having 1 to 24 carbon atoms is preferred, an alkyl group having 1 to 18 carbon atoms is more preferred, and an alkyl group having 1 to 6 carbon atoms is particularly preferred. As the alkyl group having 1 to 6 carbon atoms, there may be mentioned a methyl group, an ethyl group, an n-propyl group, an isopropyl group, an n-butyl group, a sec-butyl group, and the like. As the acyl group, a linear or branched alkanoyl group having 1 to 12 carbon atoms, an alkenylcarbonyl group, or an aroyl group is preferred and an alkanoyl group having 1 to 12 carbon atoms is particularly preferred. As the acyl group, there may be mentioned a formyl group, an acetyl group, a propionyl group, a butyryl group, and the like. As the alkoxycarbonyl group, an alkoxycarbonyl group having 2 to 13 carbon atoms in total is preferred and an alkoxycarbonyl group having 2 to 7 carbon atoms is particularly preferred. As the alkoxycarbonyl group, there may be mentioned a methoxycarbonyl group, an ethoxycarbonyl group, an n-propoxycarbonyl group, an isopropoxycarbonyl group, and the like. As the aryl group, an aryl group having 6 to 16 carbon atoms is preferred and there may be, for example, mentioned a phenyl group, a naphthyl group, and the like. As the aralkyl group, a group consisting of an aryl group having 6 to 16 carbon atoms and the above alkyl group having 1 to 6 carbon atoms is preferred and there may be, for example, mentioned a benzyl group and the like.

As the alkoxy group represented by R³, a linear or branched alkoxy group having 1 to 24 carbon atoms is preferred, an alkoxy group having 1 to 16 carbon atoms is more preferred, and an alkoxy group having 1 to 12 carbon atoms is particularly preferred. As the alkoxy group, there may be mentioned a methoxy group, an ethoxy group, an n-propoxy group, an isopropoxy group, an n-butoxy group, a sec-butoxy group, a tert-butoxy group, an n-pentyloxy group, an isopentyloxy group, a neopentyloxy group, a tert-pentyloxy group, a 2-methylbutyloxy group, an n-hexyloxy group, an isohexyloxy group, a 3-methylpentyloxy group, an ethylbutyloxy group, a cyclohexyloxy group, an octyloxy group, a decyloxy group, a dodecyloxy group, and the like. As the acyloxy group, a linear or branched alkanoyloxy group having 1 to 12 carbon atoms is preferred and an alkanoyloxy group having 1 to 6 carbon atoms is particularly preferred. As the acyloxy group, there may be mentioned an acetoxy group, a propionyloxy group, a butyryloxy group, and the like. As the alkoxycarbonyloxy group, an alkoxycarbonyloxy group having 2 to 13 carbon atoms in total is preferred and an alkoxycarbonyloxy group having 2 to 7 carbon atoms is particularly preferred. As the alkoxycarbonyloxy group, there may be mentioned a methoxycarbonyloxy group, an ethoxycarbonyloxy group, an n-propoxycarbonyloxy group, an isopropoxycarbonyloxy group, and the like. As the aryloxy group, an aryloxy group having 6 to 16 carbon atoms is preferred and there may be, for example, mentioned a phenoxy group, a naphthyloxy group, and the like. As the aralkyloxy group, the group having the above aralkyl group is preferred and there may be, for example, mentioned a benzyloxy group and the like.

In the formula (1), as $R^1$ and $R^2$, a hydrogen atom is preferred. As $R^3$, a hydroxy group, an alkoxy group, or an aralkyloxy group is preferred, a hydroxy group or an alkoxy group having 1 to 12 carbon atoms is more preferred, and a methoxy group or a hexyloxy group is particularly preferred.

As the δ-ALA derivative, δ-aminolevulinic acid methyl ester, δ-aminolevulinic acid ethyl ester, δ-aminolevulinic acid propyl ester, δ-aminolevulinic acid butyl ester, δ-aminolevulinic acid pentyl ester, δ-aminolevulinic acid hexyl ester, or the like is more preferred and δ-aminolevulinic acid methyl ester or δ-aminolevulinic acid hexyl ester is particularly preferred.

The salt of δ-ALA or a derivative thereof is not particularly limited but a pharmaceutically acceptable acid addition salt with an inorganic acid or an organic acid is preferred. As the addition salt with an inorganic acid, there may be mentioned a hydrochloride salt, a hydrobromide salt, a sulfate salt, a nitrate salt, a phosphate salt, and the like and as the addition salt with an organic acid, there may be mentioned an acetate salt, a lactate salt, a citrate salt, a tartrate salt, a succinate salt, a maleate salt, a fumarate salt, an ascorbate salt, and the like. Particularly, δ-aminolevulinic acid hydrochloride or δ-aminolevulinic acid phosphate is preferred.

δ-ALA, a derivative thereof, and a salt thereof can be produced by any method of chemical synthesis and methods using microorganisms and enzymes. For example, they can be produced by methods described in JP-A-4-9360, JP-T-11-501914, JP-A-2006-182753, JP-A-2005-314361, and JP-A-2005-314360.

In the therapeutic agent for a brain disease of the invention, (A) the above δ-ALA, a derivative thereof, or a salt thereof and (B) the iron compound are used in combination but in the diagnostic agent, the iron compound may be included. The iron compound is not particularly limited and there may be, for example, mentioned, for example, ferric chloride, iron sesquioxide, iron chlorophyllin sodium, ferritin iron, ferrous citrate, sodium iron citrate, ammonium iron citrate, ferrous fumarate, ferrous pyrophosphate, ferric pyrophosphate, saccharated iron oxide, iron acetate, iron oxalate, ferrous succinate, sodium iron succinate citrate, heme iron, dextran iron, iron lactate, ferrous gluconate, sodium iron diethylenetriaminepentaacetate, ammonium iron diethylenetriaminepentaacetate, sodium iron diethylenediaminetetraacetate, ammonium iron diethylenediaminepentatetraacetate, triethylenetetramine iron, sodium iron dicarboxymethylglutamate, ammonium iron dicarboxymethylglutamate, choline iron citrate, ferrous formate, ferric formate, ammonium ferric potassium oxalate, ferrous sulfate, ferric sulfate, ammonium iron sulfate, ferric carbonate, ferrous chloride, and iron oxide. Particularly, ferrous citrate, ferrous fumarate, ferric pyrophosphate, saccharated iron oxide, or dextran iron is preferred.

It is sufficient for the diagnostic agent for a brain disease of the invention to contain (A) the above δ-ALA, a derivative thereof, or a salt thereof, and (B) the iron compound may be used in combination. Moreover, the therapeutic agent for a brain disease of the invention is characterized by combining the component (A) and the component (B). These components (A) and (B) may be incorporated in one composition (preparation) but may be used as two kinds of preparations, i.e., a composition (preparation) containing the component (A) and a composition (preparation) containing the component (B).

The diagnostic agent and the therapeutic agent for a brain disease of the invention can be prepared by mixing (A) the above δ-ALA, a derivative thereof, or a salt thereof with a pharmaceutically acceptable carrier according to a conventional method. As forms of the agents, there may be mentioned formulations for oral administration, such as granules, fine granules, or tablets; formulations for injection, such as liquids and powders to be dissolved in use; formulations for percutaneous use, such as ointments, liquids, creams, and gels; suppositories; and the like. As forms of (B) the iron compound, there may be mentioned formulations for oral administration, such as granules, fine granules, tablets, or capsules; formulations for injection, such as liquids and powders to be dissolved in use; formulations for percutaneous use, such as ointments, liquids, creams, and gels; suppositories; and the like. Moreover, the agents may be any of the above forms containing these components (A) and (B).

The brain diseases to be targets to which the diagnostic agent and the therapeutic agent for a brain disease of the invention are any of diseases derived from mitochondrial dysfunction and there may be, for example, mentioned amyotrophic lateral sclerosis, mitochondrial encephalomyopathy, migraine, Parkinson's disease, hypoxic encephalopathy, cerebral arteriosclerosis, manic-depressive psychosis, chronic fatigue syndrome, intracranial hypertension, normal pressure hydrocephalus, cerebral vasospasm after subarachnoid hemorrhage, prevention of cerebral ischemia at surgery and intravascular surgery, atherothrombotic cerebral infarction, lacunar infarction, cardiogenic cerebral embolism, or Alzheimer's disease. Of these, atherothrombotic cerebral infarction, lacunar infarction, cardiogenic cerebral embolism, or Alzheimer's disease is particularly preferred. The more the mitochondrial activity is lowered, the more the agents are useful. Particularly, it is preferred to use the agents in an acute stage of cerebral infarction.

As administration methods of δ-ALA or a salt of a derivative thereof of the diagnostic agent and the therapeutic agent for a brain disease of the invention, there may be mentioned oral administration, intravenous administration, intramuscular administration, topical administration to the affected area, intraperitoneal administration, percutaneous administration, per-rectal administration, and the like, and intraperitoneal administration, oral administration, topical administration to the affected area, or intravenous administration is preferred. As administration methods of (B) the iron compound of the diagnostic agent and the therapeutic agent for a brain disease of the invention, there may be mentioned oral administration, intravenous administration, intramuscular administration, topical administration to the affected area, intraperitoneal administration, percutaneous administration, per-rectal administration, and the like, and intraperitoneal administration, oral administration, topical administration to the affected area, or intravenous administration is preferred.

The dosage of (A) δ-ALA or a salt of a derivative thereof of the diagnostic agent and the therapeutic agent for a brain disease of the invention varies depending on the administration method, administration route, symptoms, and body weight. In the case of oral administration, the dosage is 0.001 mg to 10 g, preferably 0.01 to 1000 mg, and particularly preferably 1 to 300 mg per kg-body weight at one dose. The dosage of (B) the iron compound of the diagnostic agent and the therapeutic agent for a brain disease of the invention varies depending on the administration method, administration route, symptoms, and body weight. In the case of oral administration, the dosage is 0.001 mg to 10 g, preferably 0.01 to 1000 mg, and particularly preferably 0.1 to 100 mg per kg-body weight at one dose.

The administration period of the therapeutic agent for a brain disease of the invention is not particularly limited so far as any therapeutic effect is exhibited and can be suitably determined in consideration of the type of the brain disease, sex, body weight, symptoms, and administration method. For example, in the case where the therapeutic agent for a brain disease of the invention is applied during an acute stage of cerebral infarction, the administration period is not limited but the agent is preferably administered within 24 hours from the onset, more preferably administered within 6 hours from the onset, and particularly preferably administered within 3 hours. Moreover, in the case where the therapeutic agent for a brain disease of the invention, it is preferred to start the administration as early as possible from the onset and it is preferred to administer the agent once a day and continue, although it depends on a recovered condition, for 2 or more days.

The therapeutic agent for a brain disease of the invention is based on the findings of the present inventors that, in a brain disease, (A) δ-ALA, a derivative thereof, or a salt thereof passes through blood-brain barrier (BBB), is accumulated in mitochondria of brain cells, and is changed to protoporphyrin IX at the site. It is known that protoporphyrin IX is excited by excitation light to emit red light. Therefore, the site where the red light is observed upon irradiation with the excitation light after the component (A) is administered can be diagnosed to be a brain disease site. On the other hand, sites which do not suffer from a brain disease do not change to red. When a brain disease site can be diagnosed during an operation, a treatment can be selectively applied to the brain disease site.

The excitation light may have any wavelength capable of observing the red light based on the excitation of protoporphyrin IX from the diseased site, and light having a wavelength of 350 to 500 nm is preferred and light having a wavelength of 390 to 420 nm is more preferred.

The wavelength of the red light to be observed is 500 to 800 nm, preferably 600 to 700 nm.

The detection method of the red light emitted from protoporphyrin IX excited by the excitation light is not particularly limited and, for example, the detection can be visually performed. Moreover, it is also possible to detect the red light by means of a detector.

After the administration of the diagnostic agent for a brain disease of the invention, the time for irradiation with the excitation light during an operation varies depending on the administration method and tissue state but is preferably about 0.1 to 10 hours where the presence of porphyrins becomes maximum and is particularly about 0.5 to 5 hours.

In the therapeutic agent for a brain disease of the invention, the reason why the mitochondrial dysfunction brain disease can be treated by the combined use of (A) δ-ALA, a derivative thereof, or a salt thereof and (B) the iron compound is not clear but may be considered that δ-ALA is accumulated at a brain disease site and changed into protoporphyrin IX and the protoporphyrin IX forms a complex with iron at the brain disease site to function as hemoglobin and cytochrome. Thereby, a mitochondrial activity is remarkably improved and, as a result, it is considered that the cell damage at the brain disease site is improved.

Therefore, in the case where the therapeutic agent for a brain disease of the invention is applied at an acute stage of cerebral infarction, it is preferred to use it in combination with a medical agent to be used for the treatment of cerebral infarction at an acute stage. As such a medical agent, there may be mentioned thrombolytic agents such as tissue plasminogen activator (t-PA), urokinase, and streptokinase; anticoagulant agents such as heparin and warfarin; antiplatelet agents such as aspirin, ticlopidine, ozagrel sodium, and cilostazol; blood diluents such as low-molecular-weight dextran; antithrombin agents such as algatoroban; anticerebral edema agents such as glyceol and mannitol; brain-protecting agents such as edaravone; and the like. Of these, the combined use with a thrombolytic agent is particularly useful in view of the re-perfusion of the blood flow at the cerebral infarction site and the accession of the therapeutic agent for a brain disease of the invention to the cerebral infarction site.

Moreover, in the invention, it is possible to diagnose mitochondrial dysfunction brain diseases by dyeing with a TTC (2,3,5-triphenyltetrazolium chloride) solution which is a mitochondria-active dyeing agent.

Specifically, a site affected by a mitochondrial dysfunction brain disease can be identified by taking out a part of the brain of an analyte, dyeing its slice with a TTC solution, taking a picture of the cut surface, and judging an area which is dyed red and has a mitochondrial activity and an area which is whitened (not dyed red) and does not have a mitochondrial activity.

For taking out a part capable of being dyed, usually, a slice is preferably prepared. The slice can be prepared by a usual method.

The concentration of the TTC solution, dyeing time, and temperature in the diagnosis of mitochondrial dysfunction brain diseases may be suitably determined so that usual diagnosis becomes possible. For example, the concentration of the TTC solution is 0.1 to 5%, preferably 0.5 to 3%, and particularly preferably 1.5 to 2.5%.

The time for dyeing (incubating) with the TTC solution is 0.1 to 4 hours, preferably 10 to 60 minutes, and particularly preferably 20 to 40 minutes.

Moreover, the temperature for dyeing with the TTC solution is 25 to 50° C., preferably 30 to 45° C., and particularly preferably 35 to 39° C.

The detection method of the red color and the white color (not dyed red) is not particularly limited and the detection can be, for example, visually performed.

According to the therapeutic agent for a brain disease of the invention, since the neurological severity score is remarkably improved even when the agent is administered after the formation of cerebral infarction, it is expected that neurological symptoms to be followed, such as consciousness disorder, movement and perception disorder, higher brain function disorder, attentiveness disorder, and emotional disorder can be recovered by the administration particularly at an acute stage of cerebral infarction.

EXAMPLES

The following will describe the invention further in detail with reference to Examples but the invention is not limited thereto.

Example 1

Preparation of Cerebral Infarction Model Rat

A nylon thread having a diameter of 1.5 mm was placed in a right middle cerebral artery of a 7-week-old male Wister rat and the blood flow was shut out for 2 hours. Thereafter, the nylon thread was removed to prepare a right middle cerebral artery-occluded model (a cerebral infarction model rat).

(Confirmation of Cerebral Infarction Model Rat)

The middle cerebral artery-occluded model rat prepared was evaluated according to NSS (Neurological Severity Scores) before preparation, immediately after preparation (0th day), and on 1st day, 3rd day, 5th day, 7th day, 10th day, and 14th day. As shown in FIG. 1, it was confirmed that the model rats prepared (6 rats) showed a severe cerebral infarction state.

TABLE 1

Neurological Severity Scores (NSS)

| | Score |
|---|---|
| Movement test | |
| When a rat is picked up with its tail, | 3 |
|   1 the rat bends its foreleg | |
|   1 the rat bends its hind leg | |
|   1 the rat moves it head in a perpendicular direction within 30 seconds (>10 seconds) | |
| When a rat is placed on a floor (normal = 0, maximum = 3), | 3 |
|   0 the rat normally walks | |
|   1 the rat cannot straightly walk | |
|   2 the rat turns to the paralyzed side | |
|   3 the rat falls down to the paralyzed side | |
| Sensory test | 2 |
|   1 stereotactic test (visual test and tactile test | |
|   2 intrinsic perceptive test (deep sensation, a leg is pressed against the edge of the table to irritate muscle of the leg) | |
| Beam balance test (normal = 0, maximum = 6), | 6 |
|   0 the rat balances in a steady stance | |
|   1 the rat grasps a side of the beam | |
|   2 the rat clings to the beam and one leg drops out of the beam | |
|   3 the rat clings to the beam and two legs drop out of the beam or turns on the beam (>60 seconds) | |
|   4 the rat intended to balance on the beam but falls down (>40 seconds) | |
|   5 the rat intended to balance on the beam but falls down (>20 seconds) | |
|   6 the rat falls down: the rat neither intends to balance nor clings to the beam (<20 seconds) | |
| Absence of reflex and movement disorder | |
|   1 auricular reflex (when an auditory canal is touched, the rat wags its head) | |
|   1 corneous reflex (when a cornea is lightly touched, the rat blinks the eye) | |
|   1 escape reflex (motor response against short noise of patting the clipboard paper) | |
|   1 stroke, myoclonus, muscular dystonia | |
| Maximum score | 18 |

When the rat cannot perform a task or a reflex tested is absent, one score is given.
13 to 18 scores: severe disorder; 7 to 12 scores: middle disorder; 1 to 6: light disorder
(Fluorescence Observation of Brain Disease Site with δ-Aminolevulinic Acid Hydrochloride)

After 6 hours, 12 hours, 24 hours, and 42 hours from the preparation of middle cerebral artery-occluded model rats, δ-aminolevulinic acid hydrochloride was dissolved in physiological saline and intraperitoneally administered to the individual model rats in an amount of 100 mg/kg-body weight of rat. After 4 hours from the administration, inside of the brain was irradiated with fluorescence of 405 nm to observe a red light site on every rat model. It was confirmed that δ-AlA was metabolized and converted into protoporphyrin IX. Moreover, it was confirmed that the red light site was in a cerebral infarction state. The same experiment was performed on normal rats but a red light site could not be confirmed even when inside of the brain was irradiated with fluorescence of 405 nm. Therefore, it was revealed that the diagnostic agent for a brain disease of the invention is a diagnostic agent capable of clearly discriminating diseased tissues and normal tissues during an operation.

(Confirmation of Mitochondrial Activity)

Figure 2:
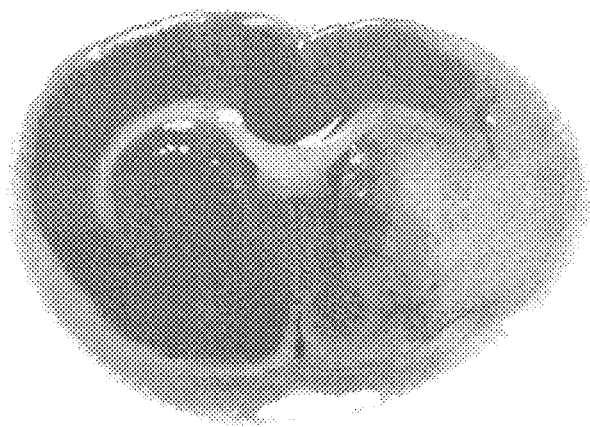
FIG. 2 is a figure showing a result of TTC dyeing of the brain of a cerebral infarction model rat.

After a rat was confirmed to be a cerebral infarction model rat based on NSS, the rat was beheaded and immediately the brain was taken out. The brain was cut in a constant section having a thickness of 2 to 3 mm by means of a razor. The slice was incubated in a TTC (2,3,5-triphenyltetrazolium hydrochloride) solution (2%), which is a mitochondria-active dyeing agent, at 37° C. for 30 minutes and immediately, a picture of the cut surface was taken to record an infarction range. From FIG. 2, it was revealed that an area which had mitochondrial activity was dyed red and an area which lacked mitochondrial activity was whitened. Thus, it was confirmed that the area where occlusion of right middle cerebral artery occurred was whitened.

Example 2

Using transient right middle cerebral artery-occluded model rats prepared in Example 1, two groups, i.e., 1) a group where 5-ALA was intraperitoneally administered immediately after the occlusion in an amount of 100 mg per kg-body weight and after 2 hours, saccharated iron oxide (trade name: FESIN) was intravenously administered in an amount of 2 mg per kg-body weight (3 rats) and 2) a group where physiological saline was intraperitoneally administered immediately after the occlusion and after 2 hours, physiological saline was intravenously administered (3 rats), were compared.

Figure 3:
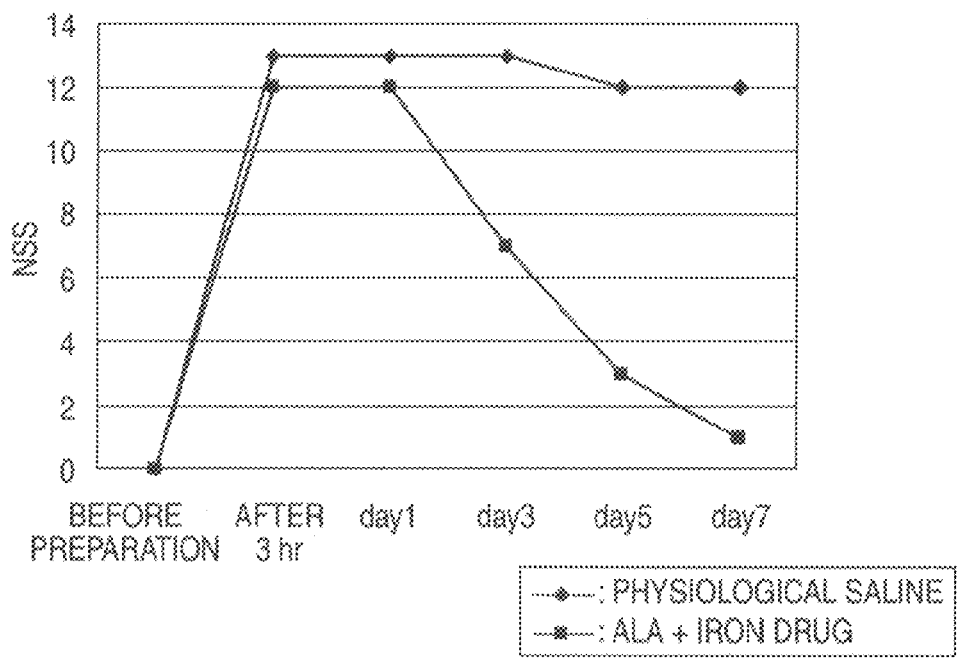
FIG. 3 is a figure showing changes of neurological severity scores in a δ-ALA and iron compound-administered group and in a physiological saline-administered group using a cerebral infarction model rat.
Figure 4:
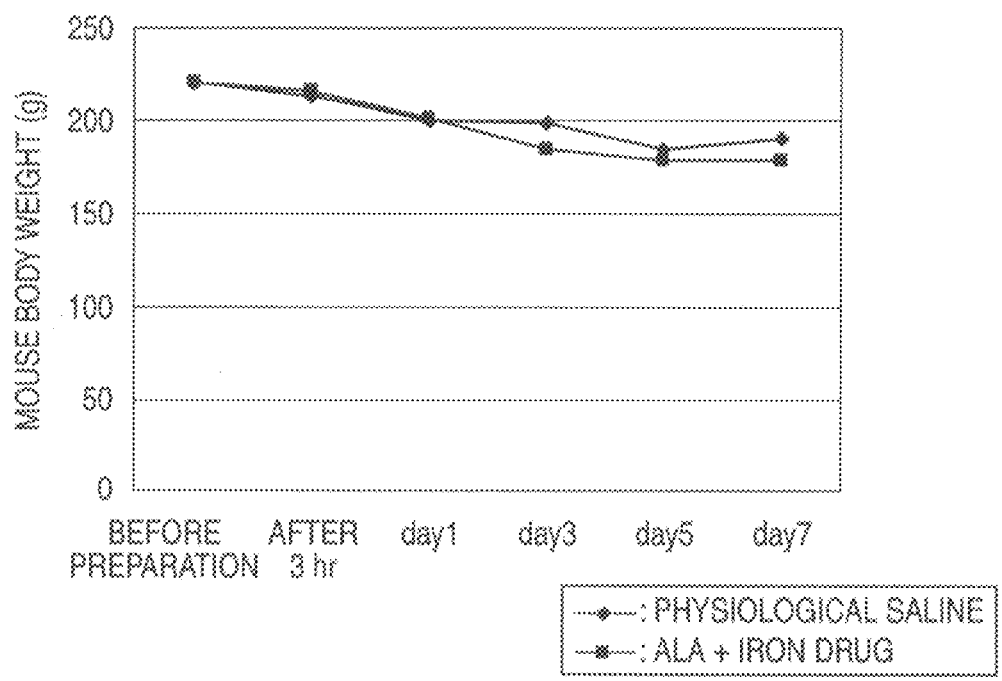
FIG. 4 is a figure showing changes of body weights in a δ-ALA and iron compound-administered group and in a physiological saline-administered group using a cerebral infarction model rat.

Before model preparation, after 3 hours, 1 day, 3 days, 5 days, and 7 days from the preparation, evaluation of NSS and measurement of body weight were performed on each rat. As shown in FIG. 3, NSS was improved to 6 to 8 scores after 3 days and progressed thereafter in the 1) group as compared with the 2) group. Moreover, with regard to the body weight, no significant difference was observed between the two groups (FIG. 4). From the above results, an effect of δ-aminolevulinic acid hydrochloride and the iron compound as a therapeutic agent for a mitochondrial dysfunction brain disease was confirmed.

While the invention has been described in detail and with reference to specific embodiments thereof, it will be apparent to one skilled in the art that various changes and modifications can be made therein without departing from the spirit and scope thereof.

The present application is based on Japanese Patent Application No. 2007-099508 filed on Apr. 5, 2007, and the contents are incorporated herein by reference.

INDUSTRIAL APPLICABILITY

According to the diagnostic agent for a mitochondrial dysfunction brain disease of the invention, a disease site can be definitely diagnosed by observing the presence of red light upon irradiation with excitation light in the event of an emergency at brain diseases such as cerebral infarction, e.g., during an operation. Moreover, according to the therapeutic agent for a mitochondrial dysfunction brain disease of the invention, by administering it after the onset of cerebral infarction, particularly in combination with thrombolytic therapy or the like, aftereffects such as consciousness disorder, movement and perception disorder, higher brain function disorder, attentiveness disorder, and emotional disorder can be improved.

The invention claimed is:

1. A method for treating a mitochondrial dysfunction brain disease selected from the group consisting of Parkinson's Disease, Alzheimer's Disease, atherothrombotic cerebral infarction, cerebral ischemia at surgery and intravascular surgery, comprising administering to a subject, an effective amount of a therapeutic agent which comprises:
   (A) a δ-aminolevulinic acid represented by the formula (1), a derivative thereof, or a salt thereof:

$$R^2R^1NCH_2COCH_2CH_2COR^3 \qquad (1)$$

wherein $R^1$ and $R^2$ each independently represents a hydrogen atom, an alkyl group, an acyl group, an alkoxycarbonyl group, an aryl group, or an aralkyl group; and $R^3$ represents a hydroxy group, an alkoxy group, an acyloxy group, an alkoxycarbonyloxy group, an aryloxy group, an aralkyloxy group, or an amino group, and (B) an iron compound.

2. The method according to claim 1, wherein (B) the iron compound is one or two or more compounds selected from ferric chloride, iron sesquioxide, iron chlorophyllin sodium, ferritin iron, ferrous citrate, sodium iron citrate, ammonium iron citrate, ferrous fumarate, ferrous pyrophosphate, ferric pyrophosphate, saccharated iron oxide, iron acetate, iron oxalate, ferrous succinate, sodium iron succinate citrate, heme iron, dextran iron, iron lactate, ferrous gluconate, sodium iron diethylenetriaminepentaacetate, ammonium iron diethylenetriaminepentaacetate, sodium iron diethylenediaminetetraacetate, ammonium iron diethylenediaminetetraacetate, triethylenetetramine iron, sodium iron dicarboxymethylglutamate, ammonium iron dicarboxymethylglutamate, choline iron citrate, ferrous formate, ferric formate, ammonium ferric potassium oxalate, ferrous sulfate, ferric sulfate, ammonium iron sulfate, ferric carbonate, ferrous chloride, and iron oxide.

3. A diagnostic method for a mitochondrial dysfunction brain disease selected from the group consisting of Parkinson's Disease, Alzheimer's Disease, atherothrombotic cerebral infarction, cerebral ischemia and intravascular surgery, which comprises:
   administering a δ-aminolevulinic acid represented by the formula (1), a derivative thereof, or a salt thereof:

$$R^2R^1NCH_2COCH_2CH_2COR^3 \qquad (1)$$

wherein $R^1$ and $R^2$ each independently represents a hydrogen atom, an alkyl group, an acyl group, an alkoxycarbonyl group, an aryl group, or an aralkyl group; and $R^3$ represents a hydroxy group, an alkoxy group, an acyloxy group, an alkoxycarbonyloxy group, an aryloxy group, an aralkyloxy group, or an amino group.

* * * * *